| United States Patent [19] | [11] Patent Number: 4,936,887 |
|---|---|
| Waldo et al. | [45] Date of Patent: Jun. 26, 1990 |

[54] DISTILLATION PLUS MEMBRANE PROCESSING OF GAS STREAMS

[75] Inventors: Richard A. Waldo; Jeffrey R. Burkinshaw, both of Bartlesville, Okla.

[73] Assignee: Phillips Petroleum Company, Bartlesville, Okla.

[21] Appl. No.: 430,554

[22] Filed: Nov. 2, 1989

[51] Int. Cl.$^5$ .............................................. F25J 3/02
[52] U.S. Cl. ........................................ 62/24; 55/74; 62/18
[58] Field of Search ............... 62/17, 18, 24, 27, 28, 62/29; 55/74

[56] References Cited

U.S. PATENT DOCUMENTS

| | | | |
|---|---|---|---|
| 3,595,782 | 7/1971 | Bucklin et al. | 208/340 |
| 4,130,403 | 12/1978 | Cooley et al. | 55/16 |
| 4,318,723 | 3/1982 | Holmes et al. | 62/20 |
| 4,350,511 | 9/1982 | Holmes et al. | 62/17 |
| 4,370,156 | 1/1983 | Goddin, Jr. et al. | 62/17 |
| 4,374,657 | 2/1983 | Schendel et al. | 62/19 |
| 4,466,946 | 8/1984 | Goddin, Jr. et al. | 62/24 |
| 4,526,594 | 7/1985 | Mehra | 62/17 |
| 4,589,896 | 5/1986 | Chen et al. | 62/28 |
| 4,595,405 | 6/1986 | Agrawal et al. | 62/18 |
| 4,654,047 | 3/1987 | Hopkins et al. | 62/24 |
| 4,654,063 | 3/1987 | Auvil et al. | 62/18 |
| 4,717,407 | 1/1988 | Choe et al. | 62/18 |
| 4,732,583 | 3/1988 | DeLong et al. | 62/24 |
| 4,817,392 | 4/1989 | Agrawal | 62/18 |

*Primary Examiner*—Ronald C. Capossela
*Attorney, Agent, or Firm*—George E. Bogatie

[57] ABSTRACT

A membrane separation is incorporated in a distillation cycle for efficient recovery of carbon dioxide from a stream containing natural gas along with carbon dioxide. Methane and carbon dioxide are separated from a feed stream in a first distillation to produce a process stream containing essentially methane and carbon dioxide and which is substantially free to ethane and higher molecular weight hydrocarbons. The process stream consisting essentially of methane and carbon dioxide is subjected to further distillation to produce a carbon dioxide-rich product stream and a process stream enriched in methane. The methane-enriched process stream is then passed to a membrane separation unit for separating methane and carbon dioxide and for producing a high purity methane product stream.

14 Claims, 1 Drawing Sheet

DISTILLATION PLUS MEMBRANE PROCESSING OF GAS STREAMS

This invention relates to separating carbon dioxide and light hydrocarbons in a gaseous stream. In one aspect it relates to a method for recovering the carbon dioxide content of a natural gas stream. In another aspect it relates to apparatus for a gas separation system utilizing both membrane and distillation techniques.

BACKGROUND OF THE INVENTION

Interest in the separation of carbon dioxide and hydrocarbons in gas streams containing a large percentage of carbon dioxide comes primarily from two areas: (1) recovery of hydrocarbons from gas streams which were previously thought uneconomical to recover, and (2) recovery of carbon dioxide from gas streams associated with enhanced oil recovery (EOR) projects employing carbon dioxide for miscible flood of oil reservoirs, thereby allowing the carbon dioxide to be reinjected into the reservoir.

Gas permeable membranes have found high volume industrial applications including gas-mixture separation, such as removal of carbon dioxide from natural gas. Other processes such as cryogenic distillation processes have been developed for separating acid gases such as carbon dioxide and hydrogen sulfide from hydrocarbons.

Although stand alone membrane separations systems and stand alone cryogenic distillation systems each provide some latitude for processing gas streams, there are inherent economic limitations to the usefulness of each technique. For example, to achieve a high purity separation in a stand alone membrane process it is generally necessary to stage multiple membrane units. In this membrane process the permeate from the first stage is compressed and fed to the second stage, thereby necessitating costly recompression of the interstage stream. Stand alone distillation processes for gaseous streams also have economic limitations. Generally distillation requires cryogenic processing for the condensation of impurities, and is considered to be economical only for processing gas streams having high $CO_2$ levels, and where the cryogenic unit does not have to produce the final product and can therefore operate at a lower purity.

Since distillation techniques for separating carbon dioxide and light hydrocarbons are generally economical for processing high carbon dioxide content gas streams, and membrane techniques are generally economical where a single stage membrane separation is employed, a separation system which includes distillation plus membrane techniques while avoiding staging of multiple membranes and cryogenic distillation of low carbon dioxide content gas streams would be highly desirable.

It is therefore an object of this invention to provide an improved method for separating carbon dioxide from light hydrocarbons in a mixture predominating in carbon dioxide.

It is a still further object of this invention to provide method and apparatus for the separation of carbon dioxide from light hydrocarbons which is effective, efficient, safe, and economical.

It is yet another object of this invention to recover a carbon dioxide stream from an EOR project which is substantially free of impurities such as methane so as to be suitable for reinjection into an oil reservoir.

BRIEF DESCRIPTION OF THE INVENTION

In accordance with the present invention there is provided method and apparatus for producing a relatively high purity stream of carbon dioxide which can, for example, be economically used in enhanced oil recovery processes such as miscible carbon dioxide flooding of oil reservoirs. The carbon dioxide stream is generally recovered from a stream containing natural gas.

The process of the present invention comprises separating ethane and higher molecular weight hydrocarbons from a feed gas stream comprising carbon dioxide, methane, ethane, and higher molecular weight hydrocarbons to produce a primary process stream consisting essentially of carbon dioxide and methane. Next a portion of the carbon dioxide contained in the primary process stream is separated from the methane to produce a carbon dioxide-rich product stream and a secondary process stream having a substantially reduced concentration of carbon dioxide relative to the concentration of carbon dioxide in the primary process stream. The secondary process stream which consists essentially of methane and carbon dioxide is then passed through a membrane separator unit to separate carbon dioxide from methane and to produce a carbon dioxide permeate stream and a methane-rich residual stream.

The apparatus of the present invention comprises a first separating means for separating ethane and higher molecular weight hydrocarbons from a feed gas stream comprising carbon dioxide, methane, ethane, and higher molecular weight hydrocarbons and for producing a primary process stream consisting essentially of carbon dioxide and methane. Operatively connected to the first separating means is a second separating means for separating a portion of the carbon dioxide from methane in the primary process stream and for producing a carbon dioxide-rich stream and a secondary process stream, wherein the secondary process stream has a substantially reduced concentration of carbon dioxide relative to the concentration of carbon dioxide in the primary process stream. Operatively connected to the second separating means is a membrane separator unit for receiving the secondary process stream and for separating carbon dioxide from methane therein, and producing a methane-rich residual stream and a carbon dioxide permeate stream. Additionally means for withdrawing the carbon dioxide permeate stream from the membrane separation unit is provided.

This invention is especially applicable to gas streams containing a large percentage of carbon dioxide, and is particularly useful when the carbon dioxide concentration is large, e.g., 80 or 90 mole percent, such as is found in gas streams produced in a carbon dioxide flood project for enhanced oil recovery. In a specific embodiment of this invention the feed gas to be separated is produced in a carbon dioxide flood project and a carbon dioxide rich stream produced by this invention is suitable for reinjection into an oil reservoir.

By operating in accordance with the present invention the economics of recovering a carbon dioxide stream, which is suitable for reinjection into an oil reservoir, is improved.

Other objects and advantages of the invention will be apparent from the foregoing brief description of the invention and the appended claims as well as from the detailed description of the preferred embodiment.

DETAILED DESCRIPTION OF THE PREFERRED EMBODIMENT

Figure 1:
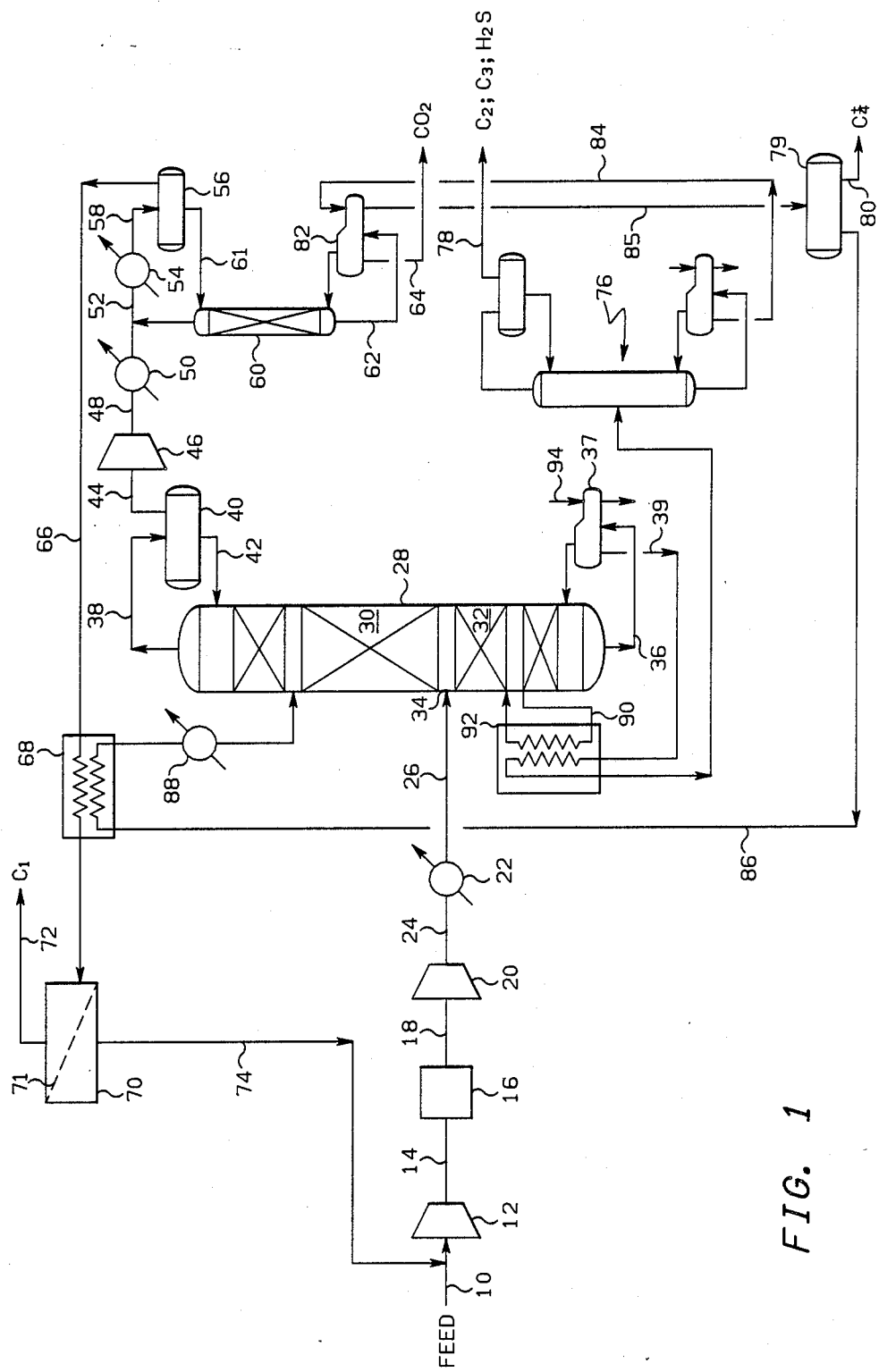
FIG. 1 is a schematic illustration of process flow for a gas plant which can be employed in the practice of this invention.

A preferred embodiment of the present invention is illustrated in FIG. 1. However, the particular flow scheme illustrated is not meant to limit the scope of the invention, since the invention is applicable to different types of fractional distillation processes which accomplish the purpose of the present invention.

Referring now to FIG. 1, a normally gaseous feedstream containing carbon dioxide, hydrogen sulfide, nitrogen and hydrocarbons is introduced into the separation system through conduit 10. The feed gas stream could have for its origin, for example a gas stream produced in an EOR project in which case it would contain a high and variable carbon dioxide loading in which the carbon dioxide content could increase to 89% or more during the life of the EOR project. Typical feed composition ranges for the feedstream introduced through conduit 10 are shown in Table 1 below:

TABLE I

| Feed Composition Ranges in Moles Percent: | |
|---|---|
| Beginning | Ending |
| 49% $C_1$ | 6% $C_1$ |
| 15% $CO_2$ | 89.3 $CO_2$ |
| 2.2% $H_2S$ | 0.3% $H_2S$ |
| 33.8% $C_{2+}$ | 4.4% $C_2S$ |

The feedstream is compressed in compressor 12 and the thus compressed feed is passed through conduit 14 to a dryer unit 16 for dehydration of the feed passing through dryer 16. The dried feed is passed from dryer 16 through conduit 18 for further compression in compressor 20. In order to obtain more efficient fractional distillation the feed is then passed from compressor 20 through heat exchanger 22 via conduit 24. The temperature of the feed is lowered substantially in heat exchanger 22 to a temperature which, together with the high pressure, will produce a fluid stream in conduit 26 comprising both liquid and vapor phases.

The feed mixture, at a temperature substantially below ambient temperature and at a pressure substantially above atmospheric pressure is fractionally distilled in column 28. Column 28, which may be a multi-tray column, a packed column, or a combination thereof, preferably comprises a rectifying zone or section 30 and a stripping zone or section 32.

The cooled compressed feedstream, comprising a mixture of carbon dioxide, hydrogen sulfide, nitrogen, and hydrocarbons, is introduced into column 28 at an intermediate point 34 preferably below the rectifying zone 30. Fractional distillation is then carried out in column 28 at a temperature of about $-35°$ F. and a pressure of about 450 psia to produce a liquid phase having a substantially increased concentration of higher boiling hydrocarbons, such as ethane, propane, and other higher molecular weight hydrocarbons relative to the concentration of the higher boiling hydrocarbons contained in the feedstream. The liquid phase is withdrawn as a bottoms stream through conduit 36.

The vapor phase, containing a substantially increased concentration of carbon dioxide, nitrogen, and methane relative to the respective concentrations of carbon dioxide, nitrogen, and methane in the feedstream, is withdrawn from fractional distillation column 28 through conduit 38, and is passed through an overhead accumulator 40. A portion of the thus withdrawn vapor is condensed in accumulator 40 and returned to column 28 through conduit 42 as a reflux.

In accordance with the presently preferred embodiment of the invention, the vapor phase passing from accumulation 40 through conduit 44 is compressed in compressor 46 and passed via conduit 48 to a heat exchanger 50 where the temperature of the vapor phase is lowered substantially so that together with the high pressure, the vapor cooled in heat exchanger 50 will produce a fluid stream in conduit 52 comprising both liquid and vapor phases. The fluid flowing in conduit 52 is further cooled in heat exchanger 54 and provided to an accumulator 56 via conduit 58. Liquid feed from accumulator 56 to distillation column 60 is provided through conduit 61. Distillation column 60 employs stripping action at a temperature of about $-35°$ F. and a pressure of about 650 psia to produce a liquid bottom stream substantially enriched in carbon dioxide relative to the feedstream to the distillation column 60 flowing in conduit 61. The carbon dioxide-rich stream is withdrawn from distillation column 60 via conduit 62 and recovered as a carbon dioxide product through conduit 64.

Further in accordance with the invention a vapor phase comprising mostly methane but having significant quantities of carbon dioxide and nitrogen and a trace quantity of hydrogen sulfide is passed from accumulator 56 via conduit 66 for indirect heat exchange in heat exchanger 68 prior to entering a membrane separation unit 70. The vapor phase flowing in conduit 66 is utilized to cool a recycle stream supplied to distillation column 28 as will be more fully explained hereinafter.

Any membrane having a different permeability for carbon dioxide than for hydrocarbons can be utilized as membrane 71 in membrane unit 70. A preferred membrane is a cellulose acetate type, however, other membranes such as polysulfone hollow fiber type could also be used. The single membrane unit 70 separates the bulk of the carbon dioxide and essentially all of the hydrogen sulfide from the hydrocarbon in the mixture flowing in conduit 66 by passing the hydrogen sulfide and carbon dioxide through membrane 71. A conduit 72 is connected to the membrane unit 70 to withdraw a high purity methane residual stream or methane-rich stream from membrane unit 70. The residual stream flowing in conduit 72 comprises mostly methane as well as impurities of nitrogen, ethane, and a possible trace of carbon dioxide. Conduit 74 is connected to the membrane unit 70 to withdraw a permeate stream containing primarily carbon dioxide and methane but having trace quantities of hydrogen sulfide. The permeate gas stream withdrawn through conduit 74 is combined with the feedstream flowing in conduit 10 to the column 28 as a recycle stream.

Further separation of the liquid phase higher boiling constituents comprising ethane and higher molecular weight hydrocarbons, which are withdrawn in a bottom stream from distillation column 28 through conduit 36, is also illustrated in FIG. 1. As illustrated, ethane, propane, higher molecular weight hydrocarbons, and hydrogen sulfide are removed in the liquid phase withdrawn from the reboiler 37 through conduit 39 by another fractional distillation step in a distillation column generally illustrated at 76, where a vapor phase of ethane and propane and a liquid phase predominating in butane and higher molecular weight hydrocarbons are produced. As illustrated, the vapor phase produced in distillation column 76 is recovered as a product through conduit 78. The liquid phase produced in distillation column 76 is utilized to supply heat to reboiler 82 associated with fractionator 60 via conduit 84 and is then provided to accumulator 79 via conduit 85. Accumulator 79 supplies a product stream through conduit 80 and a recycle stream which is provided through heat exchanger 68 via conduit 86 where the recycle stream flowing in conduit 86 is cooled in heat exchanger 68. The recycle stream flowing in conduit 86 is further cooled in heat exchanger 88 and then provided to an upper portion of distillation column 28.

In order to fractionally distill the feed mixture in fractional distillation column 28, the lower portion of the column is preferably heated in some manner. This heating can be accomplished in several different ways. As illustrated, a reboiler system is provided where heat is supplied through conduit 94. Also a side stream, which is withdrawn through conduit 90 adjacent to the bottom of distillation column 28, is passed through a side reboiler heat exchanger 92 and then back to distillation column 28 where it is reintroduced into the distillation column 28 at a point above the point of withdrawal of the side stream.

While the specific materials, and specific conditions of operation have been set forth herein by way of illustration, it is to be recognized that such specific recitations are by way of illustration only and to set forth the best mode of operation of the present invention and are not to be considered limiting.

Also reasonable variations, modifications and adaptations for various usages and conditions can be made within the scope of the disclosure and the appended claims, without departing from the scope of this invention.

That which is claimed is:

1. A process for separating components of a feed gas stream comprising carbon dioxide, hydrogen sulfide, nitrogen, methane, and higher molecular weight hydrocarbons to form a carbon dioxide-rich stream and a methane-rich stream, said process comprising the following steps:
   (a) passing said feed gas stream to a first fractional distillation column;
   (b) withdrawing a first overhead stream from said first fractional distillation column, said first overhead stream having a substantially increased concentration of carbon dioxide and methane and nitrogen relative to the respective concentrations of carbon dioxide, methane, and nitrogen in said feed gas stream;
   (c) withdrawing a first bottoms stream from said first fractional distillation column, said first bottoms stream having a substantially increased concentration of ethane and higher molecular weight hydrocarbons relative to the concentration of ethane and higher molecular weight hydrocarbons in said feed gas stream;
   (d) passing said first overhead stream to a second fractional distillation column;
   (e) withdrawing a second overhead stream wherein said second overhead stream is withdrawn from said second fractional distillation column, said second overhead stream having a substantially increased concentration of methane and nitrogen relative to the concentration of methane and nitrogen in said first overhead stream;
   (f) withdrawing a second bottoms stream wherein said second bottoms stream is withdrawn from said second fractional distillation column, and wherein said second bottoms stream forms said carbon dioxide-rich stream;
   (g) passing said second overhead stream to a membrane separation unit wherein said membrane separation unit is permeable to carbon dioxide;
   (h) withdrawing a residual gas stream from said membrane separation unit to form said methane-rich stream; and
   (i) withdrawing a residual gas stream from said membrane separation unit to form a recycle stream having a substantially increased concentration of carbon dioxide relative to the concentration of carbon dioxide in said second overhead stream.

2. A process of separating carbon dioxide from hydrocarbons comprising the following steps:
   (a) separating ethane and higher molecular weight hydrocarbons from a feed gas stream comprising carbon dioxide, methane, ethane, and higher molecular weight hydrocarbons to produce a primary process stream essentially containing carbon dioxide and methane;
   (b) separating a portion of the carbon dioxide from the methane in said primary process stream to produce a carbon dioxide-rich stream and a secondary process stream having a substantially reduced concentration of carbon dioxide relative to the concentration of carbon dioxide in said primary process stream; and
   (c) passing said secondary process stream to a membrane separation unit to separate carbon dioxide from methane and to produce a carbon dioxide permeate stream and a methane-rich residual stream.

3. A process in accordance with claim 2 wherein said feed gas stream is characterized by containing a large percentage of carbon dioxide.

4. A process in accordance with claim 2 wherein step (a) comprises the following steps:
   (a) passing said feed gas stream to a first fractional distillation column;
   (b) withdrawing an overhead stream from said first fractional distillation column to form said primary process stream; and
   (c) withdrawing a bottoms stream from said first factional distillation column, said bottom stream withdrawn from said first fractional distillation column having a substantially increased concentration of ethane and higher molecular weight hydrocarbons relative to the respective concentrations of ethane and higher molecular weight hydrocarbons in said feed gas stream.

5. A process in accordance with claim 4 wherein step (b) comprises the following steps:
   (a) passing said primary process stream to a second fractional distillation column;
   (b) withdrawing an overhead stream from said second fractional distillation column to form said secondary process stream; and
   (c) withdrawing said carbon dioxide-rich stream from said second fractional distillation column wherein said carbon dioxide-rich stream is a bottoms stream having a substantially increased concentration of carbon dioxide relative to the concentration of carbon dioxide in, said primary process stream.

6. The process of claim 4 wherein said bottom stream from said first fractional distillation column is subjected to further distillation where butane and higher molecular weight hydrocarbons are recovered therefrom and a portion of the recovered butane is recycled to said first fractional distillation column, and the remaining butane is taken as a product stream.

7. A process in accordance with claim 4 wherein said carbon dioxide permeate stream is recycled to said first fractional distillation column.

8. A process in accordance with claim 4 additionally comprising the steps of:
  (a) raising the pressure of said feed gas substantially above atmospheric pressure; and
  (b) lowering the temperature of said feed gas substantially below ambient temperature, so that said feed gas comprises both vapor and liquid phases prior to step (a).

9. Apparatus comprising:
  (a) first separating means for separating ethane and higher molecular weight hydrocarbons from a feed gas stream comprising carbon dioxide, methane, ethane, and higher molecular weight hydrocarbons and for producing a primary process stream consisting essentially of carbon dioxide and methane;
  (b) second separating means operatively connected to said first separating means for separating a portion of the carbon dioxide from methane in said primary process stream and for producing a carbon dioxide-rich stream and a secondary process stream, said secondary process stream having a substantially reduced concentration of carbon dioxide relative to the concentration of carbon dioxide in said primary process stream;
  (c) membrane separator unit means operatively connected to said second separating means for receiving said secondary process stream and for separating carbon dioxide from methane therein and producing a methane-rich residual stream and a carbon dioxide permeate stream;
  (d) means for withdrawing said methane-rich residual stream from said membrane separator unit means; and
  (e) means for withdrawing said carbon dioxide permeate stream from said membrane separator unit means.

10. Apparatus in accordance with claim 9 wherein said first separating means comprises:
  (a) a first fractional distillation column;
  (b) means for providing a feed stream to said first fractional distillation column;
  (c) overhead accumulator means operatively related to said first fractional distillation column;
  (d) means for providing a liquid reflux stream to said first fractional distillation column from said overhead accumulator means;
  (e) means for withdrawing an overhead vapor stream from said overhead accumulator means to form said primary process stream; and
  (f) means for withdrawing a liquid bottoms stream from said first fractional distillation column, said liquid bottoms stream having a substantially increased concentrations of ethane and higher molecular weight hydrocarbons relative to the respective concentrations of ethane and higher molecular weight hydrocarbons in said feed stream.

11. Apparatus in accordance with claim 10 wherein said second separating means comprises:
  (a) a second fractional distillation column;
  (b) means for providing said primary process stream as a feed stream to said second fractional distillation column;
  (c) means for withdrawing an overhead vapor stream from said second fractional distillation column to form said secondary process stream; and
  (d) means for withdrawing a liquid bottoms stream from said second fractional distillation column, said liquid bottoms stream having a substantially increased concentration of carbon dioxide relative to the concentration of carbon dioxide in said primary process stream to form said carbon dioxide-rich stream.

12. Apparatus in accordance with claim 9 additionally comprising means for recycling said carbon dioxide permeate stream to said first fractional distillation column.

13. Apparatus in accordance with claim 9 additionally comprising:
  (a) means for compressing said feed gas stream; and
  (b) means for cooling said feed gas stream so that said feed gas stream to said first fractional distillation column comprises both vapor and liquid phases.

14. Apparatus in accordance with claim 13 additionally comprising means for subjecting said bottom stream from said first fractional distillation column to further distillation to separate $C_3$ and lighter hydrocarbon components from said bottom stream from said first fractional distillation column.

* * * * *